US00PP10969P

United States Patent [19]

Austin

[11] Patent Number: Plant 10,969

[45] Date of Patent: Jun. 22, 1999

[54] SHRUB ROSE PLANT NAMED 'AUSLAND'

[75] Inventor: David Charles Henshaw Austin, Albrighton, United Kingdom

[73] Assignee: David Austin Roses Limited, Albrighton, United Kingdom

[21] Appl. No.: 08/799,096

[22] Filed: Feb. 10, 1997

[51] Int. Cl.[6] ..... A01H 5/00

[52] U.S. Cl. ..... Plt./1

[58] Field of Search ..... Plt./1, 22, 26

*Primary Examiner*—Howard J. Locker

*Attorney, Agent, or Firm*—Klarquist Sparkman Campbell Leigh & Whinston, LLP

[57] ABSTRACT

A shrub rose plant having beautiful, cupped, soft pink flowers; strong myrrh fragrance; excellent repeat flowering; and very good resistance to disease.

1 Drawing Sheet

The present invention relates to a new and distinct variety of shrub rose plant of the *Rosa hybrida* class which was originated by me by crossing an unnamed seedling with the variety Ausblush, unpatented.

The primary objective of this breeding was to produce a new shrub rose variety having great toughness and repeat flowering ability. The objective was substantially achieved, along with other desirable improvements, as evidenced by the following unique combination of characteristics that are outstanding in the new variety and that distinguish it from its parents, as well as from all other varieties of which I am aware:

1. Beautiful, cupped, soft pink flowers;
2. Strong myrrh fragrance;
3. Excellent repeat flowing; and
4. Very good disease resistance.

Asexual reproduction of this new variety by budding, as performed at Albrighton, Wolverhampton, England shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of my new rose cultivar with color descriptions using terminology in accordance with The Royal Horticultural Society (London) Colour Chart, except where ordinary dictionary significance of color is indicated.

Parentage:

*Seed parent*.—An unnamed seedling.

*Pollen parent*.—The variety Ausblush, unpatented.

Classification:

*Botanical*.—*Rosa hybrida*.

*Commercial*.—Shrub.

FLOWER

Observations made from specimens grown in a garden environment at Albrighton, Wolverhampton, England in July 1996.

Blooming habit: Recurrent.

Bud:

*Size*.—25 mm long when the petals start to unfurl.

*Form*.—The bud form is short, pointed ovoid.

*Color*.—When sepals first divide, bud color is Red-Purple Group 58D. When half blown, the upper sides of the petals are Red-Purple Group 62C; and the lower sides of the petals are Red Purple Group 62D.

*Sepals*.—Color: Yellow-Green Group 144B. Surface texture: Topsides are hairy and smooth; rough undersides. There are three normally appendaged sepals. There are two unappendaged sepals with hairy edges.

*Receptacle*.—Color: Green Group 143B. Shape: Funnel. Size: Long (about 10 mm×6 mm). Surface: Smooth; very slightly hairy.

*Peduncle*.—Length: Medium (40–45 mm). Surface: Prickly. Color: Yellow-Green Group 146B. Strength: Erect.

Bloom:

*Size*.—Medium. Average open size is 40–50 mm.

*Borne*.—Several together in flat clusters of 10 to 20 blooms.

*Stems*.—Medium, normal. Average length is about 200–400 mm. Old and new wood Yellow-Green Group 144A.

*Form*.—When first open: Cupped. Permanence: Outer petals curl back.

*Petalage*.—Number of petals under normal conditions: 45. The first flowers are very full. The second flowers have fewer petals and show stamens.

*Color*.—The upper sides of the outer petals are Red-Purple Group 56C, those of the inner petals are Red Group 63C. The reverse sides of the outer petals are Yellow Group 4B at their base, fading to white Group 155A at the edges with a hint of Red Group 56C. The reverse side of each inner petal is Red-Purple Group 65D. The major color on the upper sides is Red-Purple Group 63C.

*Variegations*.—None.

*Discoloration*.—The general tonality at the end of the first day: No change. At the end of the third day: No change.

*Fragrance*.—Strong.

Petals:

*Texture*.—Thin.

*Shape*.—Round.

*Form*.—When young, inner petals are folded but straighten out as bloom opens fully.

*Arrangement*.—Slightly quartered, globular, with no petaloids in the center.

*Persistence*.—Petals drop off cleanly before drying.

*Lastingness*.—On the plant: Long (about 5 to 6 days). As a cut flower: Fair (about 3 days).

Reproductive parts:

*Anthers*.—Size: Medium. Quantity: Many. Color: Yellow. Arrangement: Regular around styles.

*Filaments*.—Color: Yellow.

*Pollen*.—Color: Gold yellow.

*Styles*.—Color: Yellow Green Group 149D.

*Stigmas*.—Color: Yellow.

Form: Shrub.

Growth: Vigorous. Mature plant is about 75 cm in height and 60 cm in width.

Foliage:

*Number of leaflets on normal mid-stem leaves*.— 5.

*Size*.—Medium (45–60 mm long×30–40 mm wide).

*Quantity*.—Normal.

*Color*.—New foliage: Upper and lower surface: Yellow-Green Group 147A with bronzy Greyed-Purple Group 183B shading. Old foliage: Upper surface: Green Group 137A. Lower surface: Green Group 137C.

Leaflets:

*Shape*.—Broadly oval.

*Texture*.—Upper side: Leathery, slightly glossy.

*Edge*.—Serrated.

*Serration*.—Small and single.

*Petiole rachis*.—Color: Yellow-Green Group 144A.

*Petiole underside*.—With prickles.

*Stipules*.—Medium (25 mm); serrated.

*Disease resistance*.—Resistant to mildew and black-spot under normal growing conditions at Albrighton, Wolverhampton, England.

Wood:

*New wood*.—Color: Light green. Bark: Smooth.

*Old wood*.—Color: Green. Bark: Smooth.

Prickles:

*Quantity*.—On main canes from base: Ordinary. On laterals from main canes: Some few, some ordinary.

*Form*.—Medium, hooked downward.

*Color when young*.—Yellow-Green Group 146C at base and Greyed-Purple Group 187B at tip.

*Position*.—Many of the prickles are just underneath the laterals.

Small prickles:

*Quantity*.—On main stalks: Many. On laterals: Many.

*Color*.—Yellow-Green Group 146C at base and Greyed-Purple 187B at tip.

I claim:

1. A new and distinct variety of shrub rose plant of the *Rosa hybrida* class, substantially as herein shown and described, characterized particularly as to novelty by the unique combination of its beautiful, cupped, soft pink flowers; strong myrrh fragrance; excellent repeat flowering; and very good resistance to disease.

* * * * *

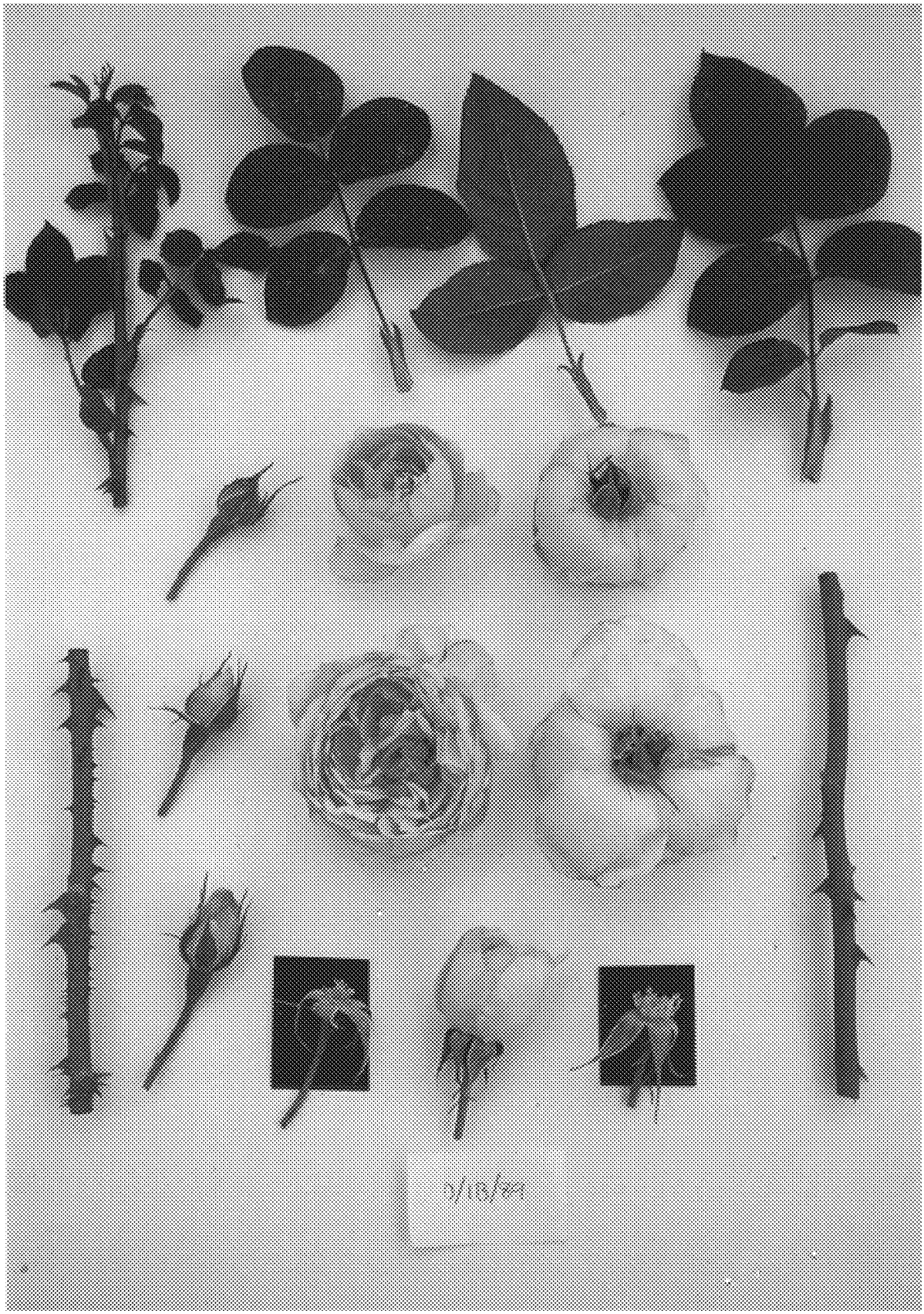
7/13/99